US009260711B2

(12) United States Patent
Lamerton et al.

(10) Patent No.: US 9,260,711 B2
(45) Date of Patent: Feb. 16, 2016

(54) SOLID MATRIX FOR ONE STEP NUCLEIC ACID AMPLIFICATION

(71) Applicant: GE HEALTHCARE UK LIMITED, Little Chalfont (GB)

(72) Inventors: Kathryn L. Lamerton, Cardiff (GB); Cheryl L. Potts, Cardiff (GB); Simon L. Stubbs, Cardiff (GB); Michael K. Kenrick, Cardiff (GB)

(73) Assignee: GE HEALTHCARE UK LIMITED, Little Chalfont (GB)

( * ) Notice: Subject to any disclaimer, the term of this patent is extended or adjusted under 35 U.S.C. 154(b) by 123 days.

(21) Appl. No.: 13/799,174

(22) Filed: Mar. 13, 2013

(65) Prior Publication Data
US 2014/0154667 A1   Jun. 5, 2014

(30) Foreign Application Priority Data
Sep. 13, 2012   (GB) .................................. 1216387.9

(51) Int. Cl.
*C12Q 1/68*   (2006.01)
*C12N 15/10*   (2006.01)

(52) U.S. Cl.
CPC .......... *C12N 15/1006* (2013.01); *C12Q 1/6848* (2013.01)

(58) Field of Classification Search
CPC ............................ C12Q 1/6848; C12N 1/1006
USPC ................. 435/6.1, 6.2, 307.1, 6.12; 422/430
See application file for complete search history.

(56) References Cited

U.S. PATENT DOCUMENTS

| 4,683,202 A | 7/1987 | Mullis |
| 5,496,562 A | 3/1996 | Burgoyne |
| 5,705,345 A | 1/1998 | Lundin et al. |

FOREIGN PATENT DOCUMENTS

| EP | 1563091 A2 | 8/2005 |
| EP | 2290099 B1 | 10/2012 |
| GB | 2346370 A | 8/2000 |
| WO | 9003959 A1 | 4/1990 |
| WO | 9102040 A1 | 2/1991 |
| WO | 9532739 A1 | 12/1995 |
| WO | 9618731 A2 | 6/1996 |
| WO | 9639813 A1 | 12/1996 |
| WO | 9938962 A2 | 8/1999 |
| WO | 0053807 A1 | 9/2000 |
| WO | 0240699 A2 | 5/2002 |
| WO | 2010066908 A1 | 6/2010 |

OTHER PUBLICATIONS

Palepu et al., "Surfactant-cyclodextrin interactions by conductance measurements", Can. J. Chem., vol. No. 66, pp. 325-328, 1988.
Valle, "Cyclodextrins and their uses: a review", Process Biochemistry, vol. No. 39, pp. 1033-1046, 2003.
Bustin et al., "Pitfalls of Quantitative Real-Time Reverse-Transcription Polymerase Chain Reaction", Journal of Biomolecular Techniques, vol. No. 15, Issue No. 3, pp. 155-166, Sep. 2004.
Baron et al., "A production system to generate reference genetic profiles from Buccal Swab cells on FTA cards", Forensic Science International: Genetics Supplement Series 3, pp. e560-e561, 2011.

*Primary Examiner* — Jezia Riley
(74) *Attorney, Agent, or Firm* — Sutherland Asbill & Brennan LLP

(57) ABSTRACT

The present invention to relates to methods and kits which can be used to amplify nucleic acids with the advantage of decreasing user time and possible contamination. The PCR reagents are bound to a solid matrix for easy processing and amplification of DNA samples.

27 Claims, 3 Drawing Sheets

SEQUENCE LISTING

```
<160> NUMBER OF SEQ ID NOS: 2

<210> SEQ ID NO 1
<211> LENGTH: 22
<212> TYPE: DNA
<213> ORGANISM: Artificial Sequence
<220> FEATURE:
<223> OTHER INFORMATION: Primer

<400> SEQUENCE: 1
ttaggcctta gcgggcttag ac                                              22

<210> SEQ ID NO 2
<211> LENGTH: 22
<212> TYPE: DNA
<213> ORGANISM: Artificial
<220> FEATURE:
<223> OTHER INFORMATION: PCR primer
```

```
<400> SEQUENCE: 2
ccaggatttt tgatgggaca cg                                          22
```

SOLID MATRIX FOR ONE STEP NUCLEIC ACID AMPLIFICATION

FIELD OF INVENTION

The present invention relates to the field of nucleic acid amplification, particularly to the use of a polymerase chain reaction to amplify nucleic acids. The invention provides methods and kits which can be used to amplify nucleic acids by embedding PCR reagents onto a solid matrix for easy amplification of DNA samples. The invention has applications in the long term storage and easy processing of nucleic acids and is particularly useful in genotyping, diagnostics and forensics.

BACKGROUND OF THE INVENTION

The polymerase chain reaction (PCR) is a common tool used in molecular biology for amplifying nucleic acids. U.S. Pat. No. 4,683,202 (Mullis, Cetus Corporation) describes a process for amplifying any desired specific nucleic acid sequence contained in a nucleic acid or mixture thereof.

Long-term storage, transport and archiving of nucleic acids on filter paper or chemically modified matrices is a well-known technique for preserving genetic material before the DNA or RNA is extracted and isolated in a form for use in genetic analysis such as PCR. Thus, EP 1563091 (Smith et al, Whatman) relates to methods for storing nucleic acids from samples such as cells or cell lysates. The nucleic acid is isolated and stored for extended periods of time, at room temperature and humidity, on a wide variety of filters and other types of solid support or solid phase media. Moreover, the document describes methods for storing nucleic acid-containing samples on a wide range of solid support matrices in tubes, columns, or multiwell plates.

WO 90/003959 (Burgoyne) describes a cellulose-based solid support for the storage of DNA, including blood DNA, comprising a solid matrix having a compound or composition which protects against degradation of DNA incorporated into or absorbed on the matrix. This document also discloses methods for storage of DNA using the solid medium, and for recovery of or in situ use of DNA.

U.S. Pat. No. 5,496,562 (Burgoyne) describes a cellulose-based solid medium and method for DNA storage. Method for storage and transport of DNA on the solid medium, as well as methods which involve either (a) the recovery of the DNA from the solid medium or (b) the use of the DNA in situ on the solid medium (for example, DNA sequence amplification by PCR) are disclosed. Unfortunately, the methods described only incorporates a surfactant or detergent on the surface of the solid medium and therefore suffer from the disadvantage that they require a separate step for the removal of the detergent before PCR is performed.

EP 2290099 B1 (Qiagen) describes again a method for processing and amplifying DNA. The method includes the steps of contacting the sample containing DNA to a solid support wherein a lysis reagent is bound to the solid support. The DNA is subsequently treated with a DNA purifying reagent and is purified. The application does not include a sequestrant on the solid support and requires a separate step for the removal of the lysis reagent and purification of the DNA before amplification.

WO 96/39813 (Burgoyne) describes a solid medium for storing a sample of genetic material and subsequent analysis; the solid medium comprising a protein denaturing agent and a chelating agent. The method described is for chelating agents which are any compound capable of complexing multivalent ions including Group II and Group III multivalent metal ions and transition metal ions. The invention does not specifically mention cyclodextrin as a chelating agent, nor does it suggest the PCR analysis could be performed in a single step.

U.S. Pat. No. 5,705,345 (Lundin et al.) describes a method of nucleic acid preparation whereby the sample containing cells is lysed to release nucleic acid and the sample is treated with cyclodextrin to neutralize the extractant. The advantage of this system is that conventional detergent removal requires a separation step however with the addition of cyclodextrin to neutralize the detergent it would remove the separation step needed and reduce chance of contamination.

GB 2346370 (Cambridge Molecular Technologies Ltd) describes applying a sample comprising cells containing nucleic acid to a filter, the cells are retained by the filter and contaminants are not. The cells are lysed on the filter and retained alongside the nucleic acid. Subsequent steps filter out the cell lysate while retaining the nucleic acid.

WO 96/18731 (Deggerdal) describes a method of isolating nucleic acid whereby the sample is bound to a solid support and sample is contacted with a detergent and subsequent steps performed to isolate the nucleic acid. The method does not include a sequestrant being bound to the solid support.

WO 00/53807 (Smith, Whatman) describes a medium for the storage and lysis of samples containing genetic material which can be eluted and analysed. The medium is coated with a lysis reagent. In addition the medium could be coated with a weak base, a chelating agent, a surfactant and optionally uric acid.

WO 99/38962 (Health, Gentra Systems Inc.) describes a solid support with a bound lysis reagent. The lysis reagent can comprise of a detergent, a chelating agent, water and optionally an RNA digesting enzyme. The solid support does not contain cyclodextrin and requires further steps for purification of the nucleic acid for amplification analysis.

WO 02/40699 (Philpott, Whatman) describes a method for the analysis of nucleic acids by applying a sample on a matrix where the matrix comprises a weak base, a chelating agent and an anionic surfactant or detergent. The suggested chelating agent was EDTA but was not limited to this embodiment. The application does not suggest that cyclodextrin as the chelating agent.

WO 91/02040 (Kosak) describes an invention using cyclodextrin-labelled primers in an amplification reaction mixture for qualitative and quantitative nucleic acid sequence analysis. The benefits were a higher signal efficiency and versatility in label colors.

WO 95/32739 (Agrawal) describes an oligonucleotide noncovalently complexed with a cyclodextrin. However the incorporation of cyclodextrin with oligonucleotides was for the cellular uptake of oligonucleotides and not for the amplification of nucleotides in a PCR reaction.

WO 2010/066908 (Beckers et al.,) describes the use of cyclodextrins to improve the specificity, sensitivity and/or yield of PCR. The method claimed is an amplification reaction which is performed in a reaction mixture comprising at least one cyclodextrin and performing the amplification reaction on said reaction. However there is no teaching of a solid matrix embedded with cyclodextrin for use in PCR amplification or a suggestion towards the combining of the solid matrix with cyclodextrin.

E. M. Martin Del Valle (Process Biochemistry, 2003, 39, 1033-1046) discloses cyclodextrins can act as molecular chelating agents and consist of six α-cyclodextrin, seven β-cyclodextrin, eight γ-cyclodextrin or more glucopyranose units linked by α-(1,4) bonds. Cyclodextrins form a hydrophilic outside which allows the molecule to dissolve in water and an apolar cavity that is hydrophobic. This cavity allows cyclodextrins to form an inclusion complex with appropriately sized non-polar moieties. The height of the cavity is the same for all types of cyclodextrin types but internal diameter and volume is determined by the number of glucose units. However the article does not explain how cyclodextrin would be considered a chelating agent.

Current methods for DNA amplification involve a DNA purification procedure which often involves several steps which increases the chance of contamination. This is a tedious process and prior art methods have a number of clear disadvantages in terms of cost, complexity and in particular, user time. For example, column-based nucleic acid purification is a typical solid phase extraction method to purify nucleic acids. This method relies on the nucleic acid binding through adsorption to silica or other support depending on the pH and the salt content of the buffer. Examples of suitable buffers include Tris-EDTA (TE) buffer or Phosphate buffer (used in DNA microarray experiments due to the reactive amines). The purification of nucleic acids on such spin columns includes a number of complex and tedious steps. Nucleic acid purification on spin columns typically involves three time-consuming and complex steps/stages: the sample containing nucleic acid is added to the column and the nucleic acid binds due to the lower pH (relative to the silanol groups on the column) and salt concentration of the binding solution, which may contain buffer, a denaturing agent (such as guanidine hydrochloride), Triton X-100, isopropanol and a pH indicator; the column is washed with 5 mM KPO4 pH 8.0 or similar, 80% EtOH); and the column is eluted with buffer or water.

Alternative methods involve the binding of nucleic acids in the presence of chaotropic agents such that DNA binds to silica or glass particles or glass beads. This property was used to purify nucleic acid using glass powder or silica beads under alkaline conditions. Typical chaotropic agents include guanidinium thiocyanate or guanidinium hydrochloride and recently glass beads have been substituted with glass containing minicolumns.

Some of the pitfalls of quantitative real-time reverse transcription polymerase chain reaction, including the effect of inhibitors, are described by Bustin & Nolan (J. Biomolecular Techniques, 2004, 15, 155-166).

The best defence against PCR amplification failure in forensics applications is to combine sound sample handling and processing techniques with extraction systems proven to efficiently purify DNA.

There is therefore a need for an improved and simplified process for performing polymerase chain reaction from samples prior to nucleic acid amplification by PCR wherein the nucleic acid is immobilised on a solid support that comprises the reagents needed for PCR amplification. The present invention addresses this problem and provides methods and kits which can be used for single step amplification of nucleic acid from solid supports, particularly cellulose-derived supports.

SUMMARY OF INVENTION

The present invention provides methods and kits which can be used to store and amplify nucleic acids by embedding PCR reagents onto a solid matrix for easy amplification of DNA samples.

According to a first aspect of the present invention there is provided a solid matrix for storing and/or amplification of nucleic acids comprising a lysis reagent and a sequestering reagent. The advantage of incorporating the lysis reagent and sequestrant on to the solid matrix is to reduce the number of steps required for nucleic acid amplification, thus saving operator time and facilitating operator usage.

In a further aspect, the nucleic acid is selected from the group consisting of DNA, RNA and oligonucleotide. The term "nucleic acid" is used herein synonymously with the term "nucleotides" and includes DNA, such as plasmid DNA and genomic DNA; RNA, such as mRNA, tRNA, sRNA and RNAi; and protein nucleic acid, PNA.

In one aspect, the lysis reagent comprises an anionic surfactant or detergent. Sodium dodecyl sulphate (SDS) is an example of an anionic surfactant frequently used to lyse biological cells.

In another aspect, the sequestering agent is a cyclodextrin. The cyclodextrin may be selected from a group consisting of α-cyclodextrin, β-cyclodextrin, γ-cyclodextrin and derivatives thereof. Cyclodextrin could consist of a group consisting of 6-O-α-D-Maltosyl-β cyclodextrin, hydroxyethyl-β-cyclodextrin, hydroxypropyl-β-cyclodextrin and 2-hydroxypropyl-β-cyclodextrin. The sequestrant is preferably α-cyclodextrin. The sequestering reagent is not a chelating agent. A chelating agent is a chemical compound that combines with a metal to form a chelate, often used to trap heavy metal ions (Colins English Dictionary, © HarperCollins Publishers 2003). One example of a lysis reagent is sodium dodecyl sulphate; sodium is a metal ion however according to Ramamurthy Palepu and Vincent C. Reinsborough (Can J. Chem Vol 66, 325-328, 1988) it is the hydrophobic tail that interacts with the cyclodextrin not the hydrophilic head.

In a further aspect, the solid matrix is selected from one of the following: glass, glass fiber, glass microfiber, silica, silica gel, silica oxide, cellulose, nitrocellulose, carboxymethylcellulose, polyester, polyamide, carbohydrate polymers, polypropylene, polytetrafluorethylene, polyvinylidinefluoride, wool or porous ceramics. The solid matrix may comprise a glass or silica-based solid phase medium, a plastics-based solid phase medium or a cellulose-based solid phase medium. The solid support is preferably a cellulose-based matrix. Examples of cellulose-based matrices include FTA™ (data file 51668), 903 neonatal cards and 31-ETF cards available from GE Healthcare.

In a further aspect, the cellulose based matrix is in the form of a pre punched disc. The cellulose based matrix can also be in the form of an FTA pre punched disc.

In one aspect, a solid matrix for storing and/or amplification of nucleic acids comprising a lysis reagent and a sequestering reagent whereby the sequestering reagent and the lysis reagent are separated physically in the matrix. The lysis reagent could also be adjacent to the sequestering reagent on said solid matrix. A spacer can be used to separate the sequestering and lysis reagent.

In one aspect the solid matrix comprising a lysis reagent and a sequestering reagent and a lyophilised or impregnated or printed Ready to Go PCR reagent for one step nucleic acid amplification wherein the Ready to Go PCR beads comprise of a DNA polymerase, deoxyribonucleotide triphosphate (dNTP), a reaction buffer and at least one primer. The advantage of dried or lyophilised formulations impregnated or printed onto to a solid matrix is that they can be easily solublised by the addition of water, thus saving operator time and facilitating operator usage.

In another aspect (10) the lysis reagent (20), sequestrant (40) and PCR reagents (50) are physically separated by a spacer (30) as demonstrated in FIG. 1A. In another aspect

(60) the lysis reagent (70), sequestrant (90) and PCR reagents (100) are physically separated by a spacer (80) as demonstrated in FIG. 1B.

According to a second aspect of the present invention, there is provided a method for amplification of nucleic acid using the polymerase chain reaction comprising the steps:
i) contacting the solid matrix containing the lysis reagent and a sequestering reagent, with a cellular sample containing nucleic acid.
ii) transferring solid matrix to a reaction vessel, and
iii) incubating the nucleic acid with a PCR reagent mixture for amplification of the nucleic acid.

The method of the invention can be used either in single tube or a high-throughput 96-well format in combination with automated sample processing as described by Baron et al., (2011, Forensics Science International: Genetics Supplement Series, 93, e560-e561). This approach would involve a minimal number of steps and increase sample throughput. The risk of operator-induced error, such as cross-contamination is also reduced since this procedure requires fewer manipulations compared to protocols associated with currently used, more labour intensive kits (e.g. QIAmp DNA blood mini kit, Qiagen). The risk of sample mix-up is also reduced since the procedure requires few manipulations Importantly, the method is readily transferable to a multi-well format for high-throughput screening. The present invention can thus improve sample storage and processing for carrying out PCR reactions to aid genetic interrogations. The invention can be conducted in a 96 well/high throughput format to facilitate sample handling and thus eliminate batch processing of samples.

In another aspect, the PCR reagents comprise a DNA polymerase, deoxyribonucleotide triphosphate (dNTP), a reaction buffer and at least one primer. The polymerase chain reaction reagent mixture can be present in a dried form, such as a "Ready-to-Go™" (RTG) format. The advantage of dried or lyophilised formulations of the polymerase chain reaction reagents is that they can be easily solublised by the addition of water, thus saving operator time and facilitating operator usage. To minimise operator error, the dried reagent mixture can be pre-dispensed into the reaction vessel, such as the well of a multi-well plate. Examples of such an RTG mixture include "Illustra Ready-to-Go RT-PCR beads" available from GE Healthcare (product code: 27-9266-01 Illustra Ready-To-Go RT-PCR Beads). These freeze-dried beads that include the reagents necessary for one-step reverse transcription-PCR, can be pre-dispensed into a reaction vessel, such as the well of a multi-well plate, as a single dose ready for use. The preformulated, predispensed, ambient-temperature-stable beads thus ensure greater reproducibility between reactions, minimize pipetting steps, and reduce the potential for pipetting errors and contamination.

According to the third aspect of the present invention there is provided a method for amplification of nucleic acid using the polymerase chain reaction comprising the steps:
i) contacting the solid matrix containing the lysis reagent and a sequestering reagent and additionally comprises lyophilised or impregnated or printed Ready to Go PCR reagent, with a cellular sample containing nucleic acid.
ii) transferring solid matrix to a reaction vessel, and
iii) incubating the nucleic acid mix with liquid water and forward and reverse primers for amplification of the nucleic acid.

In a further aspect, the reaction vessel is a well in a multi-well plate. Multi-well plates are available in a variety of formats, including 6, 12, 24, 96, 384 wells (e.g. Corning 384 well multi-well plate, Sigma Aldrich).

According to a fourth aspect of the present invention, there is provided a method of detecting the amplified nucleic acid using a detection system comprising the steps:
i) amplifying the nucleic acids using the above mentioned method.
ii) detecting the amplified nucleic acid with a computer.

The detection system can be a PCR imaging system.

In a further aspect, a method of quantifying the amplified nucleic acid using a detection system comprising the steps:
i) amplifying the nucleic acids.
ii) detecting the amplified nucleic acid using the above mentioned methods
iii) quantifying the amplified nucleic acid with a computer.

In another aspect, the sample is a cellular sample. The cellular sample may originate from a mammal, bird, fish or plant or a cell culture thereof. Preferably the cellular sample is mammalian in origin, most preferably human in origin. The cellular sample is selected from a group comprising viral, bacterial and/or tissue culture cells. The sample containing the nucleic acid may be derived from any source. This includes, for example, physiological/pathological body fluids (e.g. secretions, excretions, exudates) or cell suspensions of humans and animals; physiological/pathological liquids or cell suspensions of plants; liquid products, extracts or suspensions of bacteria, fungi, plasmids, viruses, prions, etc.; liquid extracts or homogenates of human or animal body tissues (e.g., bone, liver, kidney, etc.); media from DNA or RNA synthesis, mixtures of chemically or biochemically synthesized DNA or RNA; and any other source in which DNA or RNA is or can be in a liquid medium.

In one aspect, the nucleic acid is immobilised on the solid support for at least 24 hours. The nucleic acid may be immobilised on the solid support for longer periods, for example, for at least 7 days, for at least 30 days, for at least 90 days, for at least 180 days, for at least one year, and for at least 10 years. In this way the nucleic acid may be stored in a dried form which is suitable for subsequent analysis. Typically, samples are stored at temperatures from −200° C. to 40° C. In addition, stored samples may be optionally stored in dry or desiccated conditions or under inert atmospheres.

In one aspect, the portion is transferred to the reaction vessel by punching or cutting a disc from the solid support. Punching the portion or disc from the solid support can be effected by use of a punch, such as a Harris Micro Punch (Whatman Inc.; Sigma Aldrich)

In a further aspect, the method is for use as a tool selected from the group consisting of a molecular diagnostics tool, a human identification tool and a forensics tool.

According to a fifth aspect of the present invention, there is provided a kit for storage and amplification of nucleic acid comprising a solid support comprising a lysis reagent and a sequestering reagent and instructions for use thereof.

According to another aspect of the present invention, there is provided a kit for storing and amplifying nucleic acid comprising a solid matrix comprising a lysis reagent, a sequestering reagent and lyophilised or impregnated or printed Ready to Go PCR reagent for one step nucleic acid amplification wherein the Ready to Go PCR beads comprise of a DNA polymerase, deoxyribonucleotide triphosphate (dNTP), a reaction buffer and at least one primer and instructions for use thereof.

DETAILED DESCRIPTION OF THE INVENTION

Chemicals and Materials Used

A list of the chemicals and their sources is given below:
FTA and 31-ETF papers for storing nucleic acid were obtained from GE Healthcare UK Limited;
Normal human blood (Tissue Solutions Ltd);
Genomic DNA (Promega product code G152A);
1 kb DNA ladder (Promega product code G571A);
Harris Uni-core punch, 1.2 mm (Sigma, Catalogue number Z708860-25ea, lot 3110);
Illustra Pure Taq Ready-To-Go PCR beads (GE Healthcare UK Limited, product code 27-9557-01);
Forward and reverse β-globin primer (Sigma Genosys) (β-globin 1.3 forward 5'-TTAGGCCTTAGCGGGCTTA-GAC-3' (Seq ID No.1) and β-globin 1.3 reverse 5'-CCAG-GATTTTTGATGGGACACG-3' (Seq ID No.2));
α-cyclodextrin (Fluka code 28705) and
Sterile water (Sigma Product code W4502).

Experimental Results

DNA Measurement from Dried Blood Spots from Cellulose Matrices Using qPCR

The standard well of the 96 well PCR plate was loaded with 5 μl of the 1 Kb DNA ladder with 1 μl of 6× loading buffer.

The control lane was prepared using ing genomic DNA in the presence of 1.25% liquid α-cyclodextrin.

Samples were combined with forward and reverse β-globin primer (10 pmoles/μl), α-cyclodextrin (10%) and sterile water for a final volume of 25 μl. The 25 μl sample mix was added to each well of a 96 well PCR plate containing 1 Pure Taq Ready-To-Go PCR bead prior to amplification for a final volume of 25 μl.

PCR reaction was set up as follows:
25 μl total volume per well; 25 μl mixture of primers, sterile water and/or liquid α-cyclodextrin and Pure Taq Ready-To-Go PCR bead. Standards and samples were added to the appropriate wells. The plates are centrifuged at 1000 rpm for 1 minute and sealed. PCR was carried out on an MJ Research PTC-200 Thermo Cycler following the manufactures' user instructions.

The thermal cycling conditions were: 95° C. for 5 min, 95° C. for 30 sec, 55/65° C. for 1 min, 72° C. for 2 min followed by 35 cycles of: 95° C. for 30 sec, 55/65° C. for 1 min, 72° C. 2 min, followed by 72° C. for 10 mins. Following amplification, visualisation of PCR products was achieved using agarose gel electrophoresis (1×TAE buffer, 1% agarose gel). The results are presented graphically in FIGS. 2 and 3.

Figure 1A:
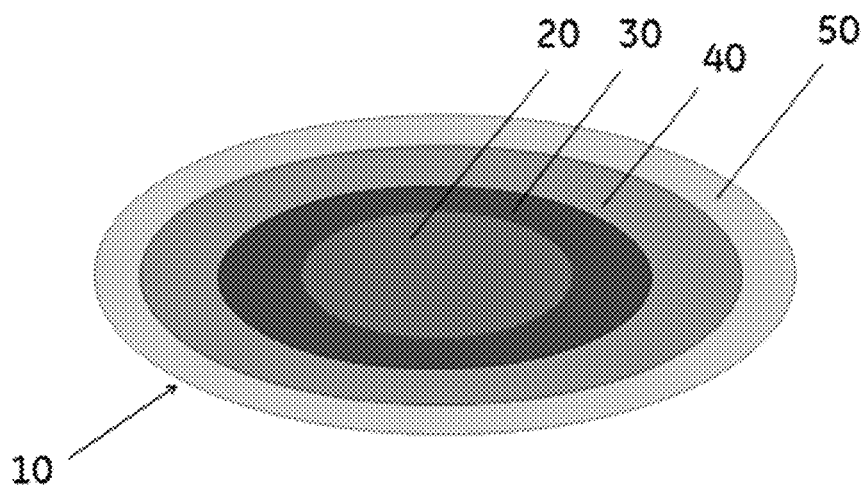
FIG. 1A shows a configuration of a solid matrix (10) whereby the lysis reagent (20), sequestrant (40) and PCR reagents (50) are physically separated by a spacer (30).
Figure 1B:
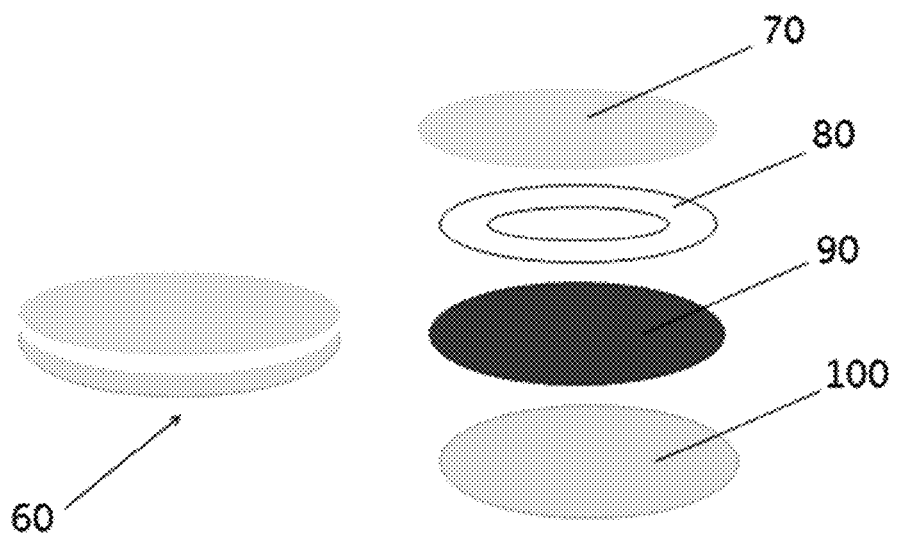
FIG. 1B shows a configuration of a solid matrix (60) whereby the lysis reagent (70), sequestrant (90) and PCR reagents (100) are physically separated by a spacer (80).
Figure 2:
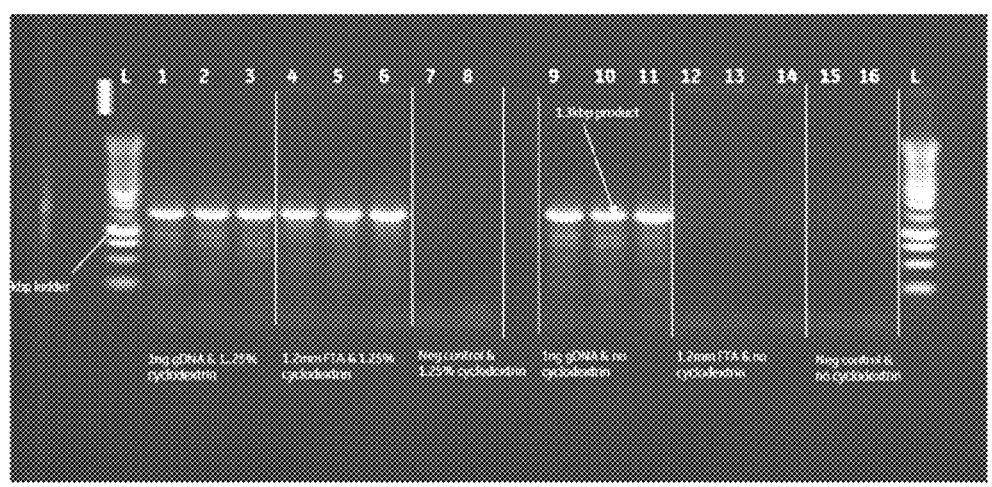
FIG. 2 shows the results from PCR amplification of unwashed blood-spotted FTA with or without liquid α-cyclodextrin treatment.

In the FIG. 2 experiment 65 μl aliquots of normal human blood were applied to FTA and were allowed to dry. 1.25% liquid α-cyclodextrin was added to the PCR reactions. Punches (1.2 mm diameter) were extracted from the FTA (±normal human blood) using the Harris Uni-core punch (Sigma). The punch was then added to the appropriate PCR well along with the reaction mix.

FIG. 2 shows PCR results of unwashed blood-spotted FTA with or without liquid α-cyclodextrin treatment: Lane 1-3: purified genomic DNA with liquid cyclodextrin; Lane 4-6: punch spotted with whole blood (1.2 mm) with liquid cyclodextrin; Lane 7-8: no DNA template with cyclodextrin; Lane 9-11: purified genomic DNA without cyclodextrin; Lane 12-14: punch spotted with whole blood (1.2 mm) without cyclodextrin; Lane 15-16: no DNA template or cyclodextrin.

FIG. 2 presents DNA levels obtained from dried blood spots treated with or without cyclodextrin using endpoint PCR. As can be seen, high yields of nucleic acid were obtained from liquid cyclodextrin treated blood spotted FTA samples but PCR was inhibited in the absence of cyclodextrin on blood spotted FTA samples.

TABLE 1

Concentration of reagents in lanes 1 to 16 of FIG. 2.

| | | Reagent Concentration | Final Concentration in 25 μl reaction |
|---|---|---|---|
| Lane 1 to 3 | Forward Primer | 10 pmoles/μl | 0.2 pmoles/μl |
| | Reverse Primer | 10 pmoles/μl | 0.2 pmoles/μl |
| | α-cyclodextrin (liquid) | 10% | 1.25% |
| | Genomic DNA | 1 ng/μl | 1 ng/μl |
| | Sterile Water | 19.88 μl | 19.88 μl |
| | Illustra Pure Taq RTG PCR bead | 1 bead | 1 bead |
| Lane 4 to 6 | Forward Primer | 10 pmoles/μl | 0.2 pmoles/μl |
| | Reverse Primer | 10 pmoles/μl | 0.2 pmoles/μl |
| | α-cyclodextrin (liquid) | 10% | 1.25% |
| | Blood-spotted FTA punch | 1.2 mm punch | 1.2 mm punch |
| | Sterile Water | 20.88 μl | 20.88 μl |
| | Illustra Pure Taq RTG PCR bead | 1 bead | 1 bead |
| Lane 7 to 8 | Forward Primer | 10 pmoles/μl | 0.2 pmoles/μl |
| | Reverse Primer | 10 pmoles/μl | 0.2 pmoles/μl |
| | α-cyclodextrin (liquid) | 10% | 1.25% |
| | Genomic DNA | — | — |
| | Sterile Water | 20.88 μl | 20.88 μl |
| | Illustra Pure Taq RTG PCR bead | 1 bead | 1 bead |
| Lane 9 to 11 | Forward Primer | 10 pmoles/μl | 0.2 pmoles/μl |
| | Reverse Primer | 10 pmoles/μl | 0.2 pmoles/μl |
| | α-cyclodextrin (liquid) | — | — |
| | Genomic DNA | 1 ng/μl | 1 ng |
| | Sterile Water | 23 μl | 23 μl |
| | Illustra Pure Taq RTG PCR bead | 1 bead | 1 bead |
| Lane 12 to 14 | Forward Primer | 10 pmoles/μl | 0.2 pmoles/μl |
| | Reverse Primer | 10 pmoles/μl | 0.2 pmoles/μl |
| | α-cyclodextrin (liquid) | — | — |
| | Blood-spotted FTA punch | 1.2 mm punch | 1.2 mm punch |
| | Sterile Water | 24 μl | 24 μl |
| | Illustra Pure Taq RTG PCR bead | 1 bead | 1 bead |
| Lane 15 to 16 | Forward Primer | 10 pmoles/μl | 0.2 pmoles/μl |
| | Reverse Primer | 10 pmoles/μl | 0.2 pmoles/μl |
| | α-cyclodextrin (liquid) | — | — |
| | Genomic DNA | — | — |
| | Sterile Water | 24 μl | 24 μl |
| | Illustra Pure Taq RTG PCR bead | 1 bead | 1 bead |

Figure 3:
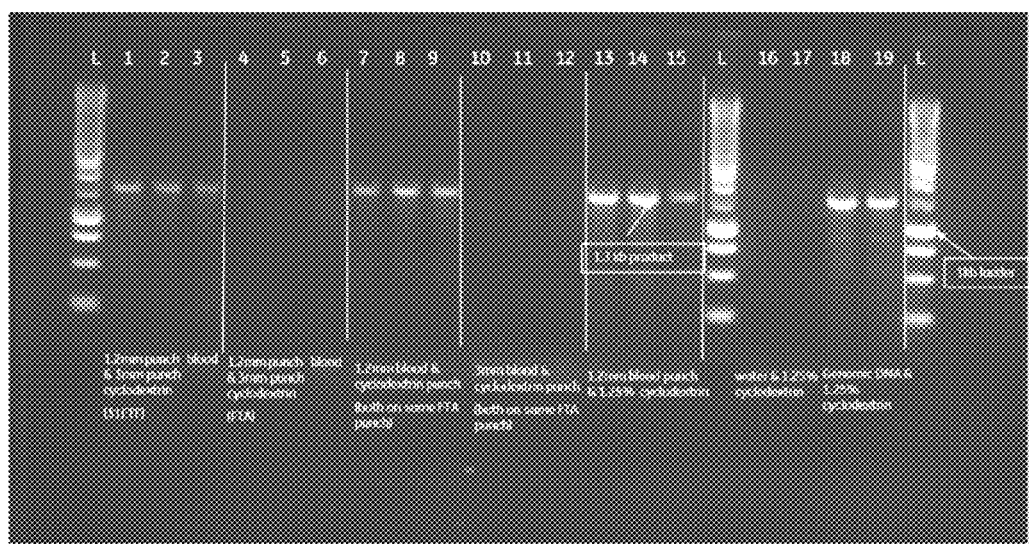
FIG. 3 shows the results from PCR amplification of unwashed blood-spotted FTA combined with a α-cyclodextrin spotted sample paper.

In the FIG. 3 experiment 65 μl aliquots of normal human blood were applied to FTA and were allowed to dry and 10% liquid α-cyclodextrin was applied to 31-ETF (final concentration of 1.2%). Or FTA was pre-spotted with 10% cyclodextrin and dried prior to the addition of blood. Punches (1.2 mm diameter of FTA and 3 mm diameter of 31-ETF) were extracted from each paper type (±normal human blood) using the Harris Uni-core punch. Both punches were added to the PCR well along with the reaction mix.

FIG. 3 shows PCR results of unwashed blood-spotted FTA with or without α-cyclodextrin treated 31-ETF: Lane 1-3: blood spotted FTA (1.2 mm) with cyclodextrin spotted 31-ETF (3 mm); Lane 4-6: blood spotted FTA (1.2 mm diameter punch) with cyclodextrin spotted 31-ETF (3 mm); Lane 7-9: blood spotted and cyclodextrin spotted FTA (1.2 mm diameter punch); Lane 10-12: blood spotted and cyclodextrin spotted FTA (3 mm diameter punch); Lane 13-15: blood spotted FTA (1.2 mm diameter) with liquid cyclodextrin added; Lane 16-17 no DNA template; Lane 18-19: purified genomic DNA with 1.25% liquid cyclodextrin.

FIG. 3 presents DNA levels obtained using endpoint PCR from blood spotted FTA combined with cyclodextrin treated 31-ETF; or cyclodextrin pretreated FTA which was then treated with a blood sample. As can be seen, high yields of nucleic acid were obtained from the combination of blood spotted FTA samples combined with cyclodextrin treated 31-ETF.

TABLE 2

Concentration of reagents in lanes 1 to 19 of FIG. 3.

| | | Reagent Concentration | Final Concentration in 25 µl reaction |
|---|---|---|---|
| Lane 1 to 3 | Forward Primer | 10 pmoles/µl | 0.2 pmoles/µl |
| | Reverse Primer | 10 pmoles/µl | 0.2 pmoles/µl |
| | α-cyclodextrin 31-ETF punch | 3 mm punch (excess SDS) | 1.2% |
| | Blood spotted FTA punch | 1.2 mm punch | 1.2 mm punch |
| | Sterile Water | 24 µl | 24 µl |
| | Illustra Pure Taq RTG PCR bead | 1 bead | 1 bead |
| Lane 4 to 6 | Forward Primer | 10 pmoles/µl | 0.2 pmoles/µl |
| | Reverse Primer | 10 pmoles/µl | 0.2 pmoles/µl |
| | α-cyclodextrin FTA punch | 3 mm punch (excess SDS) | 1.2% |
| | Blood spotted FTA punch | 1.2 mm punch | 1.2 mm punch |
| | Sterile Water | 24 µl | 24 µl |
| | Illustra Pure Taq RTG PCR bead | 1 bead | 1 bead |
| Lane 7 to 9 | Forward Primer | 10 pmoles/µl | 0.2 pmoles/µl |
| | Reverse Primer | 10 pmoles/µl | 0.2 pmoles/µl |
| | α-cyclodextrin FTA punch combined with blood | 1.2 mm punch | 1.2 mm punch |
| | Sterile Water | 24 µl | 24 µl |
| | Illustra Pure Taq RTG PCR bead | 1 bead | 1 bead |
| Lane 10 to 12 | Forward Primer | 10 pmoles/µl | 0.2 pmoles/µl |
| | Reverse Primer | 10 pmoles/µl | 0.2 pmoles/µl |
| | α-cyclodextrin FTA punch combined with blood | 3 mm punch (excess SDS) | 1.2% |
| | Sterile Water | 24 µl | 24 µl |
| | Illustra Pure Taq RTG PCR bead | 1 bead | 1 bead |
| Lane 13 to 15 | Forward Primer | 10 pmoles/µl | 0.2 pmoles/µl |
| | Reverse Primer | 10 pmoles/µl | 0.2 pmoles/µl |
| | α-cyclodextrin (liquid) | 10% | 1.25% |
| | Blood spotted FTA punch | 1.2 mm punch | 1.2 mm punch |
| | Sterile Water | 20.88 µl | 24 µl |
| | Illustra Pure Taq RTG PCR bead | 1 bead | 1 bead |
| Lane 16 to 17 | Forward Primer | 10 pmoles/µl | 0.2 pmoles/µl |
| | Reverse Primer | 10 pmoles/µl | 0.2 pmoles/µl |
| | α-cyclodextrin (liquid) | 10% | 1.25% |
| | Genomic DNA | — | — |
| | Sterile Water | 20.88 µl | 20.88 µl |
| | Illustra Pure Taq RTG PCR bead | 1 bead | 1 bead |
| Lane 18 to 19 | Forward Primer | 10 pmoles/µl | 0.2 pmoles/µl |
| | Reverse Primer | 10 pmoles/µl | 0.2 pmoles/µl |
| | α-cyclodextrin (liquid) | 10% | 1.25% |
| | Genomic DNA | 1 ng/µl | 1 ng |
| | Sterile Water | 19.88 µl | 19.88 µl |
| | Illustra Pure Taq RTG PCR bead | 1 bead | 1 bead |

While preferred illustrative embodiments of the present invention are described, one skilled in the art will appreciate that the present invention can be practised by other than the described embodiments, which are presented for the purposes of illustration only and not by way of limitation. The present invention is limited only by the claims that follow.

What is claimed is:

1. A solid matrix for storing and/or amplification of nucleic acids comprising a solid matrix, wherein the matrix comprises a lysis reagent and a sequestering reagent, and wherein the matrix comprises both the lysis reagent and the sequestering reagent before the matrix has any contact with a nucleic acid.

2. The solid matrix of claim 1, wherein said lysis reagent comprises an anionic surfactant or detergent.

3. The solid matrix of claim 2, wherein said anionic surfactant is sodium dodecyl sulphate (SDS).

4. The solid matrix of claim 1, wherein said sequestering agent is a cyclodextrin.

5. The solid matrix of claim 4, wherein the cyclodextrin is selected from the group consisting of α-cyclodextrin, β-cyclodextrin, and γ-cyclodextrin.

6. The solid matrix of claim 4, wherein the cyclodextrin is α-cyclodextrin.

7. The solid matrix of claim 4, wherein the cyclodextrin is selected from the group consisting of 6-O-α-D-Maltosyl-β-cyclodextrin, hydroxyethyl-β-cyclodextrin, hydroxypropyl-β-cyclodextrin and 2-hydroxypropyl-β-cyclodextrin.

8. The solid matrix of claim 1, wherein the solid matrix comprises a glass or silica-based solid phase medium, a plastics-based solid phase medium or a cellulose-based solid phase medium.

9. The solid matrix of claim 8, wherein the solid phase medium is selected from one of the following: glass, glass fiber, glass microfiber, silica, silica gel, silica oxide, cellulose, nitrocellulose, carboxymethylcellulose, polyester, polyamide, carbohydrate polymers, polypropylene, polytetrafluorethylene, polyvinylidinefluoride, wool or porous ceramics.

10. The solid matrix of claim 1, wherein the solid matrix is a cellulose based matrix.

11. The solid matrix of claim 10, wherein said cellulose based matrix is in the form of a pre punched disc.

12. The solid matrix of claim 10, wherein said cellulose based matrix is in the form of a pre punched disc having a cellulose based matrix and comprising a protein denaturing agent and a chelating agent.

13. The solid matrix of claim 1, wherein the sequestering reagent and the lysis reagent are separated physically in the matrix.

14. The solid matrix of claim 13, wherein the lysis reagent is adjacent to the sequestering reagent on said solid matrix.

15. The solid matrix of claim 13, wherein the sequestering reagent and the lysis reagent are separated by a spacer.

16. The solid matrix of claim 1, further comprising lyophilised or impregnated or printed Ready to Go PCR reagents for one step nucleic acid amplification, wherein the Ready to Go PCR reagents comprise a DNA polymerase, a deoxyribonucleotide triphosphate (dNTP), a reaction buffer, and at least one primer.

17. The solid matrix of claim 16, wherein the lysis reagent, the sequestering reagent, and the Ready to Go PCR reagents are physically separated by a spacer.

18. A method for amplification of nucleic acid using polymerase chain reaction comprising the steps:
 i) contacting the solid matrix of claim 1 with a cellular sample containing nucleic acid;
 ii) transferring the solid matrix to a reaction vessel; and
 iii) incubating the nucleic acid with a PCR reagent mixture for amplification of the nucleic acid.

19. The method of claim 18, wherein said PCR reagent mixture comprises a DNA polymerase, a deoxyribonucleotide triphosphate (dNTP), a reaction buffer, and at least one primer.

20. A method for amplification of nucleic acid using polymerase chain reaction comprising the steps:
 i) contacting the solid matrix of claim 16 with a cellular sample containing nucleic acid;
 ii) transferring the solid matrix to a reaction vessel; and
 iii) incubating nucleic acid with liquid water and forward and reverse primers for amplification of the nucleic acid.

21. A method of detecting amplified nucleic acid using a detection system comprising the steps:
 i) amplifying nucleic acids using the method of claim 18; and
 ii) detecting the amplified nucleic acids with a computer.

22. The method of claim 21, wherein the detecting step is performed using a PCR imaging system.

23. The method of claim 18, wherein the cellular sample is selected from a group comprising a virus, a bacteria and tissue culture cells.

24. A kit for storing and amplifying nucleic acid comprising the solid matrix of claim 1 and instructions for use thereof.

25. A kit for storing and amplifying nucleic acid comprising the solid matrix of claim 16 and instructions for use thereof.

26. A method of detecting the amplified nucleic acid using a detection system comprising the steps:
 i) amplifying nucleic acids using the method of claim 20; and
 ii) detecting the amplified nucleic acid with a computer.

27. The method of claim 20, wherein the cellular sample is selected from a group comprising a virus, a bacteria and tissue culture cells.

* * * * *